(12) United States Patent
Prohaska

(10) Patent No.: US 8,475,783 B2
(45) Date of Patent: Jul. 2, 2013

(54) APPARATUS AND METHOD FOR GENERATING CARBON DIOXIDE AS AN ATTRACTANT FOR BITING ARTHROPODS

(76) Inventor: John Prohaska, Millbury, MA (US)

(*) Notice: Subject to any disclaimer, the term of this patent is extended or adjusted under 35 U.S.C. 154(b) by 44 days.

(21) Appl. No.: 13/311,466

(22) Filed: Dec. 5, 2011

(65) Prior Publication Data
US 2013/0142753 A1    Jun. 6, 2013

(51) Int. Cl.
*A01N 25/00* (2006.01)
(52) U.S. Cl.
USPC .......................................................... 424/84
(58) Field of Classification Search
None
See application file for complete search history.

(56) References Cited

U.S. PATENT DOCUMENTS

| | | | |
|---|---|---|---|
| 5,633,224 A * | 5/1997 | Porter | 510/444 |
| 6,305,122 B1 * | 10/2001 | Iwao et al. | 43/112 |
| 2004/0128902 A1 * | 7/2004 | Kollars, Jr. et al. | 43/107 |
| 2012/0124890 A1 * | 5/2012 | Hainze | 43/121 |
| 2012/0246998 A1 * | 10/2012 | Vasudeva et al. | 43/114 |

* cited by examiner

*Primary Examiner* — James H Alstrum Acevedo
*Assistant Examiner* — Thor Nielsen
(74) *Attorney, Agent, or Firm* — The Patent Practice of Szmanda & Shelnut, LLC; Charles R. Szmanda; James G. Shelnut

(57) ABSTRACT

Disclosed and claimed herein is a device and method for generating carbon dioxide as an attractant for biting arthropods in combination with a trap, comprising: a reaction chamber charged with an aqueous acid solution when in use; a gas outlet from the reaction chamber connecting between the reaction chamber and the trap; a feeder reservoir containing a powder when in use, said powder comprising a bicarbonate salt; and means for controllably adding the powder to the reaction chamber; whereby carbon dioxide is generated in the reaction chamber, passed through the outlet and into the trap.

20 Claims, 2 Drawing Sheets

US 8,475,783 B2

APPARATUS AND METHOD FOR GENERATING CARBON DIOXIDE AS AN ATTRACTANT FOR BITING ARTHROPODS

FIELD OF THE INVENTION

The present application for patent is in the field of attracting biting arthropods for the purpose of trapping them. More particularly, disclosed and claimed herein are an apparatus and a method for providing carbon dioxide and other attractants to an arthropod trap.

BACKGROUND

Mosquitoes, flies, ticks, fleas and chiggers are arthropods that carry a wide range of blood borne diseases which readily infect humans and animals when bitten. These diseases include among other things, lyme disease, ehrlichiosis, tularemia, vectored borreliosis (Masters disease), encephalitis, West Nile virus, Dengue Fever, malaria and others.

Bedbugs of genus the Cimex, particularly the species *lectularius* and *hemipterus*, are small crawling blood-sucking insects that feed on human, bird and bat blood. In humans, bedbugs rarely appear as the result of a lack of hygiene. Rather, bedbugs now appear more and more frequently in resort hotels, motels, apartments, college dormitories, cruise ships and airplanes.

In past years, the widespread use of insecticides such as DDT and other pesticides resulted in a drastic decline the populations of these pests. However, many biting arthropods have developed a resistance to insecticides. Moreover, these chemicals frequently pose a threat to humans and other non targeted animals.

Efforts to trap mosquitoes, biting flies, ticks, fleas, chiggers, biting midges, bedbugs and other biting arthropods have used a number of techniques including sticky paper, electrostatic traps and physical traps, sprays and chemical attractants. Of the latter, carbon dioxide has been used alone or in combination with certain organic chemicals, in combination with insect traps, to increase trapping efficiency by attracting insects to the vicinity of the trap.

Various attempts to provide carbon dioxide as a means of attracting biting arthropods have been made. For example in U.S. Patent Application No. 2009/0145019, Nolan et al. disclose a bedbug trap fitted with "a tank containing compressed $CO_2$ .... The carbon dioxide source preferably emits $CO_2$ via an outlet positioned proximate to [a] heating source." [drawing references omitted] However, although the disclosed apparatus of Nolan is capable of releasing carbon dioxide controllably and over sustained periods, a pressurized tank of $CO_2$ is quite heavy. The trap and tank are, therefore not transported and set up easily. In addition, mechanical breaching of the high pressure carbon dioxide tank may result in an explosion.

In U.S. Pat. No. 4,506,473, Waters discloses a trap in which a "carbonate salt," including a bicarbonate salt is brought into contact with a reservoir of aqueous acid solution. However while this apparatus is lighter and more transportable than that disclosed in Nolan, the carbonate salt and acid solution are disclosed to be brought together all at once by breaching a bladder and allowing the contents of separated chambers to mix, thus resulting in the evolution of a large amount of gas over a short period of time. Such a method is unsuitable for sustained trapping operation, which requires release of carbon dioxide over a period of hours or days. Further, the rate of carbon dioxide release should be controllable to accommodate the individual characteristics of the target biting arthropod.

In U.S. Pat. No. 6,920,716, Kollars et al. disclose a non-electrical carbon dioxide generating arthropod trap. In this disclosure the combination of baking soda and vinegar is used to generate carbon dioxide gas with the optional addition of urea, lactic acid, and ammonia as further attractants. In this device the dry sodium bicarbonate powder (baking soda) is placed in a separate reactor container and aqueous solution of ascetic acid (vinegar) is dripped into the reactor container to produce carbon dioxide. However, this method of mixing the reactants leads to powder caking and inconsistent gas flow rates.

Therefore, there remains a need for an easily transportable trap, fitted with a carbon dioxide generator capable of controllably releasing carbon dioxide. These needs are addressed in the subject matter disclosed and claimed herein.

DETAILED DESCRIPTION

Figure 1:
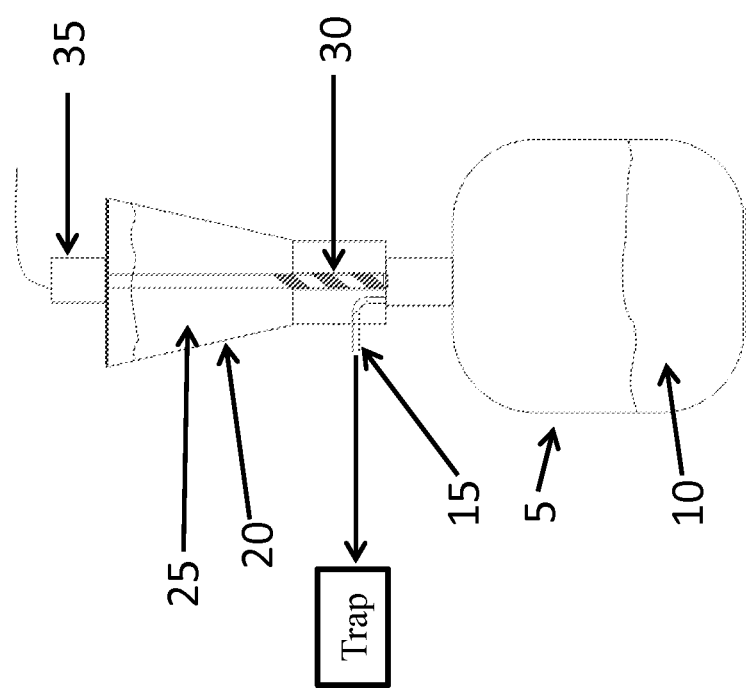
FIG. 1 illustrates an embodiment of the improved carbon dioxide generation apparatus.

As used herein, the conjunction "and" is intended to be inclusive and the conjunction "or" is not intended to be exclusive unless otherwise indicated. For example, the phrase "or, alternatively" is intended to be exclusive.

As used herein, the term "biting arthropods" is understood to describe members of the phylum Arthropoda that feed on the blood of warm blooded animals. Without limitation, these include members of the class Insecta, such as mosquitoes, bedbugs, biting flies, biting midges, fleas, gnats, and the like. Further, and without limitation, the term "biting arthropods" is understood to include members of the class Arachnida such as ticks, chiggers, mites and the like.

As used herein, the term "aqueous acid solution" is understood to contain water and an acid and may further contain, without limitation, dissolved gasses, salts, surfactants and other soluble and insoluble matter.

Disclosed herein is a device for generating carbon dioxide as an attractant for biting arthropods in combination with a trap, comprising: a reaction chamber charged with an aqueous acid solution when in use; a gas outlet from the reaction chamber connecting between the reaction chamber and the trap; a feeder reservoir containing a powder when in use, said powder comprising a bicarbonate salt; and means for controllably adding the powder from the feeder reservoir to the reaction chamber; whereby carbon dioxide is generated in the reaction chamber, passed through the outlet and into the trap.

Further disclosed herein is an improved arthropod trap for catching biting arthropods assisted by the evolution of carbon dioxide, the improvement comprising: a reaction chamber charged with an aqueous acid solution when in use; a gas outlet from the reaction chamber connecting between the reaction chamber and the trap; a feeder reservoir containing a powder when in use, said powder comprising a bicarbonate salt; and means for controllably adding the powder from the feeder reservoir to the reaction chamber; whereby carbon dioxide is generated in the reaction chamber, passed through the outlet and through or into vicinity of the trap.

Further disclosed herein is an improved method of generating carbon dioxide as an attractant for biting arthropods connected to an insect trap, the improvement comprising: providing a reaction chamber charged with an aqueous acid solution; providing a gas outlet from the reaction chamber for connecting between the reaction chamber and the trap; providing a feeder reservoir containing a powder, said powder comprising a bicarbonate salt; and providing means for controllably adding the powder from the feeder reservoir to the reaction chamber; wherein carbon dioxide is generated in the reaction chamber, passed through the outlet and into the trap.

Further disclosed herein is an improved method of generating carbon dioxide as an attractant for biting arthropods connected to an insect trap, the improvement comprising: providing a reaction chamber charged with an aqueous acid solution; providing a gas outlet from the reaction chamber for connecting between the reaction chamber and the trap; providing a feeder reservoir containing a powder, said powder comprising a bicarbonate salt; and providing means for controllably adding the powder from the feeder reservoir to the reaction chamber; wherein carbon dioxide is generated in the reaction chamber, and passed through the outlet and through or into vicinity of the trap.

The particular trap used may be selected to correspond to the characteristics of the targeted biting arthropods. For example, crawling insects may be capable of crawling on a smooth surface into the trap or their journey into the trap may be facilitated by a textured surface. On the other hand, flying insects may be trapped more effectively within a trap equipped with an electric fan that tends to encourage entry but discourage exit. Many trap configurations are available. Without limitation these may include nets, Bates type stable traps, cylindrical lard can traps, No. 10 Trinidad traps, Trueman & McIver ramp traps, plexiglas traps, DeFoliant & Morris conical traps, malaise traps, carbon dioxide light traps, Fay-Prince carbon dioxide trap, sticky traps such as flypaper, New Jersey light traps, ACIS traps (Army Collapsible Insect Surveillance), CDC light traps, Kimsey & Chaniotis traps, EVS light traps, Monk's Wood light traps, U.S. Army solid state light traps (AMSS), Pfuntner light traps, star beam sticky light traps, cylindrical light traps, updraft light traps, "Nozawa" traps, "AS" traps, UV light traps, Flashing light traps, non-electrical light traps, Haufe & Burgess traps, Fay-Prince trap, Wilton & Kloter cylinder traps, duplex cone traps, Ikeshoji cylinder sound traps, Ikeshoji & Ogawa cup trap, Kanda et al. cylinder and lantern traps, heat traps, bag traps, and sugar-base attraction traps. The method for generating carbon dioxide may be a separate unit or may be incorporated as a part of the trap assembly.

The feeder reservoir can be any container suitable for containing a solid material such as the powder comprising a bicarbonate salt. Such a feeder reservoir may include, without limitation, a conical or funnel shaped structure, a hopper structure or the like. Moreover, the feeder can be at an arbitrary angle, for example a pin feeder, a volumetric feeder or a piston feeder can deliver the powder comprising a bicarbonate salt to the reaction vessel at arbitrary angles.

The powder comprising a bicarbonate salt may include bicarbonates such as alkali metal bicarbonates, alkaline earth metal bicarbonates, other metal bicarbonates, bicarbonate salts wherein the counter ion is a protonated organic primary, secondary or tertiary amine, a bicarbonate salt wherein the counter ion is the ammonium ion or other suitable ion. For example and without limitation, the powder comprising a bicarbonate salt may contain a bicarbonate salt, chosen from sodium bicarbonate, lithium bicarbonate, potassium bicarbonate, ammonium bicarbonate, magnesium bicarbonate, calcium bicarbonate strontium bicarbonate or combinations thereof. In cases where ammonium bicarbonate is used, it may be advantageous to provide an opening to the outside air in the feeder reservoir. This will allow the escape of ammonia gas from the decomposition of ammonium bicarbonate to water, carbon dioxide and ammonia. Nitrogen containing compounds such as ammonia, urea and certain ammonium compounds are believed to attract certain biting arthropods.

Further, the powder comprising a bicarbonate salt may contain carbonate salts as additives to control the flow of carbon dioxide. These may include without limitation, a carbonate salt chosen from sodium carbonate, lithium carbonate, potassium carbonate, ammonium carbonate, magnesium carbonate, calcium carbonate strontium carbonate or combinations thereof.

The powder comprising a bicarbonate salt may further comprise additives that permit flow of the powder in humid conditions. These include anti caking agents such as silicon dioxide, aluminum oxide, boron nitride, calcium chloride, magnesium sulfate, calcium bentonite, sodium bentonite, sodium alumino-silicate, magnesium carbonate, calcium silicate, tricalcium phosphate, talc, kaolin, starch, cellulose or combinations thereof.

In addition to adding, anti caking agents to the powder comprising a bicarbonate salt, an effective method of preventing caking is to heat the powder before it is released into the reaction vessel. Temperatures from 20° C.-35° C. may be used.

In the instant application, means and their equivalents for controllably adding the powder comprising a bicarbonate salt to the reaction chamber are suitably fitted to the feeder reservoir. Such means may be used to add the solid slowly or rapidly in a manner designed to produce carbon dioxide at a rate effective to attract the targeted biting arthropod. Further, the powder may be added at an approximately constant rate or in pulsed fashion, for example, to simulate breathing. Pulsed powder feeding may be characterized by a full stop between individual pulsed additions or by a background addition during which intermittent increases or decreases occur. Such means for controllably adding the powder comprising a bicarbonate salt to the reaction chamber include but are not limited to constant rate and pulsed auger feeders, pin feeding and volumetric dispensing feeders, pour feeders, and vibro feeders, all available from Labman Automation, Ltd, of Stokesley, North Yorkshire, UK. In addition, combinations thereof and equivalents of the foregoing may be used. Other suitable means and their equivalents for controllably adding the powder comprising a bicarbonate salt to the reaction chamber include piston feeders, pneumatic feeders, centrifugal feeders, electrostatic feeders, and conveyor belt feeders, equivalents thereof or combinations thereof with any of the foregoing.

The aqueous acid charged into the acid chamber may include, without limitation, acetic acid, ascorbic acid. butanoic acid, citric acid, formic acid, heptanoic acid, hexanoic acid, 1-octanoic acid, lactic acid, octanoic acid, oxalic acid, pentanoic acid, propanoic acid, uric acid, succinic acid, malonic acid, maleic acid, citriconic acid, norbornene dicarboxylic acid, gamma-hydroxy butanoic acid, benzoic acid, boric acid sulfuric acid, hydrochloric acid, nitric acid, phosphoric acid, linear or branched $C_1$-$C_{20}$ alkane sulfonic acids, linear or branched $C_2$-$C_{20}$ alkene sulfonic acids, $C_6$-$C_{20}$ substituted or unsubstituted aryl sulfonic acids or combinations thereof. In addition, any of the foregoing acids may be used in combination with other acids. Such acids may be present in amounts effective to attract the targeted biting arthropod[s].

The reaction chamber, initially containing the aqueous acid solution, can be any container capable of holding an aqueous solution. Such a container may be configured with a stopper or cover that permits the powder comprising a bicarbonate salt to be dispensed and the carbon dioxide controllably released. Such systems are known in the art. In addition, transport of the reaction chamber can be accomplished with a separate cover. Further, both the reaction chamber and the feeder reservoir can be flexible bags coupled together with means for dispensing the powder comprising the bicarbonate salt. The openings to those bags can be clamped shut or sealed to avoid spillage before and after use.

The gas outlet may be configured above the reaction mixture in such a way as to avoid portions of the reaction mixture coming out of the gas outlet. This might include a filter, such as a paper, cellulose fiber or sand filter or the like. In addition, the gas outlet may include a one-way valve or other controller such as one or more holes to control the flow of the product carbon dioxide gas.

Organic biting arthropod attractants may be useful in attracting targeted biting arthropods to the trap in addition to the carbon dioxide generated as described above. Without limitation, these include 6-methyl-3,5-heptadiene, 1,1,2-trichloroethane, 1,1,3-trichloroacetone, 1,1-trichloroethane, 1,4-diaminobutane, 1,4-diaminobutane, 1-heptene, 1-methylpyrrole, 1-nonene, 1-octanol, 2-octanol, 3-octanol, 4-octanol, 1-octen-3-one, 1-octene, 1-penten-3-one, 2,3-butanedione, 2,3-hexanedione, 2-amino-pyridine, 2-decanone, 2-heptanone, 2-hexanone, 2-methyl-3-pentanone, 2-methylfuran, 2-nonanone, 2-nonanone, 1-octanol, 2-octanone, 2-pentanone, 3,4-hexanedione, 3-buten-2-one, 3-heptanone, 3-hexanone, 3-hydroxy-2-butanone, 3-methyl-2-pentanone, 3-nonanone, 3-nonen-2-one, 3-octene-2-ol, 3-pentanone, 3-penten-2-one, 4-decanone, 4-heptanone, 4-hexen-3-one, 4-methyl-2-pentanone, 5-methyl-3-hexen-2-one, 5-nonanone, 6-methyl-5-hepten-2-one, acetaldehyde, acetonitrile, acetphenone, benzaldehyde, benzonitrile, bromoform, butanal, butanone, buten-2-one, carbon disulfide, carbon tetrachloride, chloroform, diethyl disulfide, diethyl ether, diethyl phthalate, dimethoxymethane, dimethyl disulfide, dimethyl trisulfide, dimethylsulfoxide, ethanol, ethyl lactate, ethyl pyruvate, ethylvinyl sulfide, formaldehyde, furfuryl alcohol, indole, isobutanal, isoprene, linalool, methanol, methyl butyrate, methyl lactate, methyl pyruvate, methyl-2-hexanone, methyl-3-octanone, methylene chloride, methylpropyl disulfide, nonanal, octene, p-cresol, phenylacetonitrile, phorone, pinene, propanoic acid, tetrachloroethylene, thiolactic acid, thiophene, thiourea, toluene, turpentine, and combinations thereof. The foregoing can be incorporated into the powder containing a carbonate salt as described supra or mixed into the aqueous acid in the reaction chamber. Acidic biting arthropod attractants may be used, either as additives or as major constituents of the aqueous acid solution. These include octanoic acid, lactic acid, propanoic acid, butanoic acid or the like.

As noted previously, the non acidic biting arthropod attractors, described supra, may be incorporated into the powder comprising a bicarbonate salt. Addition of these materials may be accomplished conveniently by adsorbing them on the anti caking agents before blending them with the bicarbonate and other ingredients. Adsorption of these materials may be done from the vapor or liquid phases. It is sometimes, though not always effective to dehydrate the anti caking agent by heating or other suitable means before the one or more biting arthropod attractors are introduced. Dehydration may be accomplished simply by passing dry nitrogen through the anti caking agent for 1-5 hours or by baking at 50° C. to 100° C. for 1-5 hours.

Example 1

A device was constructed for generating carbon dioxide to be used with a trap was constructed in accordance with the diagram of FIG. 1. Shown are a reaction chamber, 5, charged with an aqueous acid solution, 10, a gas outlet from the reaction chamber, 15, connecting between the reaction chamber and the trap, a feeder reservoir, 20, containing a powder comprising a bicarbonate salt, 25, and means for controllably adding the powder from the feeder reservoir to the reaction chamber, in the case of this particular embodiment, an auger feeder, 30, controlled by an electronic controller, 35.

In the embodiment of this example, the reaction chamber, 5, was charged with about 1.5 L. of water and about 400 g of citric acid and the feeder reservoir, 20, was charged with about 500 g of sodium bicarbonate. In operation, the electronic controller, 35, was used to vary the addition rate of the sodium bicarbonate to the reaction chamber via the auger feeder, 30.

Example 2

Figure 2:
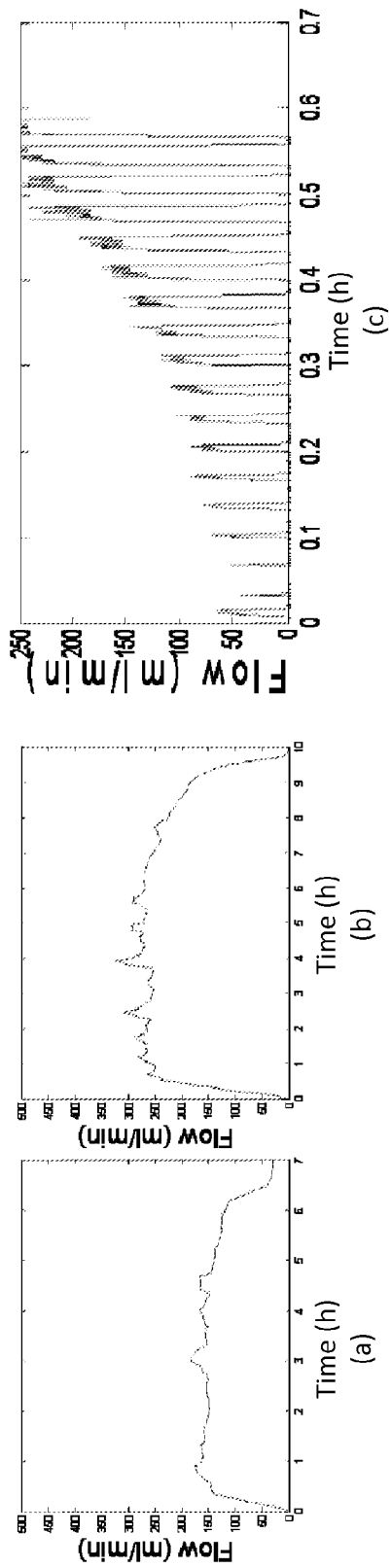
FIG. 2 illustrates controlled delivery of carbon dioxide using the apparatus of FIG. 1 adjusted as described herein, infra.

The apparatus of Example 1 was used to generate carbon dioxide by adjusting the auger feeder to deliver about 0.56 g/min of sodium bicarbonate continuously to the reaction chamber containing the aqueous citric acid solution. The gas flow rate was monitored by a calibrated MEMS flow meter, available from Omron Corporation of Yasu, Shiga Prefecture, Japan. The result is as shown in FIG. 2(a). As can be seen, the targeted flow rate of 150 mL/min was maintained over a time of about 6 hours.

Example 3

As in Example 2, except that the initial charges of sodium bicarbonate and citric acid were about 650 g 600 g, respectively and the auger feeder controller was adjusted to deliver about 1.04 g/min of sodium bicarbonate to the reaction chamber. The result is as shown in FIG. 2(b). As can be seen, the targeted flow rate of 275 mL/min was maintained over a time of about 8.5-9 hours.

Example 4

As in Example 2, except that the initial water charge in the reaction chamber was 1.25 L and the auger feeder controller was adjusted to deliver sodium bicarbonate intermittently according to Table 1, wherein the duty cycle is the quotient of the "ON" time and the period. Results are as shown in FIG. 2(c). As can be seen, the carbon dioxide flow corresponds to the introduction of sodium bicarbonate in the reaction vessel. Moreover, as the duty cycle is increased, the flow rate of carbon dioxide increases accordingly. Variation of this kind can be used, for example to simulate breathing and may be useful in attracting some target biting arthropods.

TABLE 1

| | $CO_2$ Pulse Schedule | | |
|---|---|---|---|
| Pulse # | ON (sec) | OFF (sec) | Duty Cycle |
| 0 | 30 | 120 | 0.2 |
| 1 | 5 | 115 | 0.042 |
| 2 | 10 | 110 | 0.083 |
| 3 | 15 | 105 | 0.125 |
| 4 | 20 | 100 | 0.167 |
| 5 | 25 | 95 | 0.208 |
| 6 | 30 | 90 | 0.25 |
| 7 | 35 | 85 | 0.292 |
| 8 | 40 | 80 | 0.333 |
| 9 | 45 | 75 | 0.375 |
| 10 | 50 | 70 | 0.417 |

TABLE 1-continued

CO₂ Pulse Schedule

| Pulse # | ON (sec) | OFF (sec) | Duty Cycle |
|---------|----------|-----------|------------|
| 11 | 55 | 65 | 0.458 |
| 12 | 60 | 60 | 0.5 |
| 13 | 65 | 55 | 0.542 |
| 14 | 70 | 50 | 0.583 |
| 15 | 75 | 45 | 0.625 |
| 16 | 80 | 40 | 0.667 |
| 17 | 85 | 35 | 0.708 |

Example 5

As in Example 2, except that the sodium bicarbonate was delivered at 0.94 g·min so as to give a carbon dioxide flow rate of 250 mL/min. The gas outlet was coupled to a CDC-type mosquito trap, available from the John W. Hock Company of Gainesville Fla., and allowed to collect mosquitoes for 12 hours. For comparison, a similar trap but with carbon dioxide from a tank was placed about 100 m away. Sites were selected so as to provide a testing area that is known to be infested by mosquitoes and to provide similar terrain. In the comparison apparatus care was taken to use the same carbon dioxide flow rate. Results were recorded repetitively over 9 non-consecutive days and are shown in Table 2.

TABLE 2

| Date | CO₂ Gas Tank | CO₂ Apparatus Example 5 |
|------|--------------|-------------------------|
| Jun. 23, 2010 | 99 | 102 |
| Jun. 29, 2010 | 34 | 183 |
| Jul. 8, 2010 | 73 | 41 |
| Jul. 12, 2010 | 49 | 118 |
| Jul. 14, 2010 | 14 | 15 |
| Jul. 15, 2010 | 73 | 41 |
| Jul. 20, 2010 | 53 | 57 |
| Aug. 2, 2010 | 12 | 6 |
| Aug. 5, 2010 | 1 | 1 |
| Total collected | 408 | 564 |

As can be seen from Table 2, the apparatus of the present example compares favorably with the apparatus wherein carbon dioxide is supplied by a tank. While even minor differences in terrain habitat and micro climate may influence mosquito populations, it is known that certain mosquitoes will travel long distances in search of a blood meal.

Although the present invention has been shown and described with reference to particular examples, various changes and modifications which are obvious to persons skilled in the art to which the invention pertains are deemed to lie within the spirit, scope and contemplation of the subject matter set forth in the appended claims.

What is claimed is:

1. A device for generating carbon dioxide as an attractant for biting arthropods in combination with a trap, comprising:
   a. a reaction chamber charged with an aqueous acid solution when in use;
   b. a gas outlet from the reaction chamber connecting between the reaction chamber and the trap;
   c. a feeder reservoir containing a powder when in use, said powder comprising a bicarbonate salt; and
   d. means for controllably adding the powder from the feeder reservoir to the reaction chamber;
   whereby carbon dioxide is generated in the reaction chamber, passed through the outlet and into the trap.

2. The device of claim 1, wherein the aqueous solution comprises one or more acids, wherein at least one of the one or more acids is chosen from acetic acid, ascorbic acid, butanoic acid, citric acid, formic acid, heptanoic acid, hexanoic acid, 1-octanoic acid, lactic acid, octanoic acid, oxalic acid, pentanoic acid, propanoic acid, uric acid, succinic acid, malonic acid, maleic acid, citriconic acid, norbornene dicarboxylic acid, gamma-hydroxy butanoic acid, benzoic acid, boric acid sulfuric acid, hydrochloric acid, nitric acid, phosphoric acid, linear or branched $C_1$-$C_{20}$ alkane sulfonic acids, linear or branched $C_2$-$C_{20}$ alkene sulfonic acids, $C_6$-$C_{20}$ substituted or unsubstituted aryl sulfonic acids or combinations thereof.

3. The device of claim 1, further comprising a means for sealing the reaction chamber to prevent spillage of an aqueous solution during transport.

4. The device of claim 1, wherein the means for controlled delivery of the solid are configured to deliver the solid in either pulsed or uniform fashion.

5. The device claim 1, wherein the means for controllably adding the powder to the reaction chamber are adjustable.

6. The device of claim 1, wherein the powder comprising a bicarbonate salt comprises a bicarbonate salt, chosen from sodium bicarbonate, lithium bicarbonate, potassium bicarbonate, ammonium bicarbonate, magnesium bicarbonate, calcium bicarbonate strontium bicarbonate or combinations thereof.

7. The device of claim 1, wherein the solid powder comprising a bicarbonate salt further comprises a carbonate salt chosen from sodium carbonate, lithium carbonate, potassium carbonate, ammonium carbonate, magnesium carbonate, calcium carbonate strontium carbonate or combinations thereof.

8. The device of claim 1, wherein the solid powder comprising a bicarbonate salt further comprises an anti caking agent; said anti caking agent comprising a material chosen from silicon dioxide, aluminum oxide, boron nitride, calcium chloride, magnesium sulfate, calcium bentonite, sodium bentonite, sodium alumino-silicate, magnesium carbonate, calcium silicate, tricalcium phosphate, talc, kaolin, starch, cellulose or combinations thereof.

9. The device of claim 1, wherein the powder further comprises an organic insect attractant, chosen from 6-methyl-3,5-heptadiene, 1,1,2-trichloroethane, 1,1,3-trichloroacetone, 1,1-trichloroethane, 1,4-diaminobutane, 1,4-diaminobutane, 1-heptene, 1-methylpyrrole, 1-nonene, 1-octanol, 2-octanol, 3-octanol, 4-octanol, 1-octen-3-one, 1-octene, 1-penten-3-one, 2,3-butanedione, 2,3-hexanedione, 2-amino-pyridine, 2-decanone, 2-heptanone, 2-hexanone, 2-methyl-3-pentanone, 2-methylfuran, 2-nonanone, 2-nonanone, 1-octanol, 2-octanone, 2-pentanone, 3,4-hexanedione, 3-buten-2-one, 3-heptanone, 3-hexanone, 3-hydroxy-2-butanone, 3-methyl-2-pentanone, 3-nonanone, 3-nonen-2-one, 3-octene-2-ol, 3-pentanone, 3-penten-2-one, 4-decanone, 4-heptanone, 4-hexen-3-one, 4-methyl-2-pentanone, 5-methyl-3-hexen-2-one, 5-nonanone, 6-methyl-5-hepten-2-one, acetaldehyde, acetonitrile, acetphenone, benzaldehyde, benzonitrile, bromoform, butanal, butanone, buten-2-one, carbon disulfide, carbon tetrachloride, chloroform, diethyl disulfide, diethyl ether, diethyl phthalate, dimethoxymethane, dimethyl disulfide, dimethyl trisulfide, dimethylsulfoxide, ethanol, ethyl lactate, ethyl pyruvate, ethylvinyl sulfide, formaldehyde, furfuryl alcohol, indole, isobutanal, isoprene, linalool, methanol, methyl butyrate, methyl lactate, methyl pyruvate, methyl-2-hexanone, methyl-3-octanone, methylene chloride, methylpropyl disulfide, nonanal, octene, p-cresol, phenylacetonitrile, phorone, pinene, tetrachloroethylene, thiolactic acid, thiophene, thiourea, toluene, turpentine, or combinations thereof.

10. The device of claim 1, wherein the aqueous acid solution further comprises an organic insect attractant, chosen from 6-methyl-3,5-heptadiene, 1,1,2-trichloroethane, 1,1,3-trichloroacetone, 1,1-trichloroethane, 1,4-diaminobutane, 1,4-diaminobutane, 1-heptene, 1-methylpyrrole, 1-nonene, 1-octanol, 2-octanol, 3-octanol, 4-octanol, 1-octen-3-one, 1-octene, 1-penten-3-one, 2,3-butanedione, 2,3-hexanedione, 2-amino-pyridine, 2-decanone, 2-heptanone, 2-hexanone, 2-methyl-3-pentanone, 2-methylfuran, 2-nonanone, 2-nonanone, 1-octanol, 2-octanone, 2-pentanone, 3,4-hexanedione, 3-buten-2-one, 3-heptanone, 3-hexanone, 3-hydroxy-2-butanone, 3-methyl-2-pentanone, 3-nonanone, 3-nonen-2-one, 3-octene-2-ol, 3-pentanone, 3-penten-2-one, 4-decanone, 4-heptanone, 4-hexen-3-one, 4-methyl-2-pentanone, 5-methyl-3-hexen-2-one, 5-nonanone, 6-methyl-5-hepten-2-one, acetaldehyde, acetonitrile, acetphenone, benzaldehyde, benzonitrile, bromoform, butanal, butanone, buten-2-one, carbon disulfide, carbon tetrachloride, chloroform, diethyl disulfide, diethyl ether, diethyl phthalate, dimethoxymethane, dimethyl disulfide, dimethyl trisulfide, dimethylsulfoxide, ethanol, ethyl lactate, ethyl pyruvate, ethylvinyl sulfide, formaldehyde, furfuryl alcohol, indole, isobutanal, isoprene, linalool, methanol, methyl butyrate, methyl lactate, methyl pyruvate, methyl-2-hexanone, methyl-3-octanone, methylene chloride, methylpropyl disulfide, nonanal, octene, p-cresol, phenylacetonitrile, phorone, pinene, propanoic acid, tetrachloroethylene, thiolactic acid, thiophene, thiourea, toluene, turpentine or combinations thereof.

11. A method of generating carbon dioxide as an attractant for biting arthropods connected to an insect trap, comprising:
   a. providing a reaction chamber charged with an aqueous acid solution;
   b. providing a gas outlet from the reaction chamber for connecting between the reaction chamber and the trap;
   c. providing a feeder reservoir containing a powder, said powder comprising a bicarbonate salt; and
   d. providing means for controllably adding the powder from the feeder reservoir to the reaction chamber;
wherein carbon dioxide is generated in the reaction chamber, passed through the outlet and into the trap.

12. The method of claim 11, wherein the means for controllably adding the powder to the reaction chamber are adjustable.

13. The method of claim 11, wherein the aqueous acid solution, comprises one or more acids chosen from acetic acid, ascorbic acid. butanoic acid, citric acid, formic acid, heptanoic acid, hexanoic acid, lactic acid, octanoic acid, oxalic acid, pentanoic acid, propanoic acid, uric acid, succinic acid, malonic acid, maleic acid, citriconic acid, norbornene dicarboxylic acid, gamma-hydroxy butanoic acid, benzoic acid, boric acid sulfuric acid, hydrochloric acid, nitric acid, phosphoric acid, linear or branched $C_1$-$C_{20}$ alkane sulfonic acids, linear or branched $C_2$-$C_{20}$ alkene sulfonic acids, $C_6$-$C_{20}$ substituted or unsubstituted aryl sulfonic acids or combinations thereof.

14. The method of claim 11, further comprising providing a means for sealing the reaction chamber to prevent spillage of an aqueous solution.

15. The method of claim 11, wherein the means for controlled delivery of the solid are configured to deliver the solid in either pulsed or uniform fashion.

16. The method of claim 11, wherein the bicarbonate salt is chosen from sodium bicarbonate, lithium bicarbonate, potassium bicarbonate, ammonium bicarbonate, magnesium bicarbonate, calcium bicarbonate strontium bicarbonate or combinations thereof.

17. The method of claim 11, wherein the powder further comprises a carbonate salt chosen from sodium carbonate, lithium carbonate, potassium carbonate, ammonium carbonate, magnesium carbonate, calcium carbonate strontium carbonate or combinations thereof.

18. The method of claim 11, wherein the powder further comprises an organic insect attractant, chosen from 6-methyl-3,5-heptadiene, 1,1,2-trichloroethane, 1,1,3-trichloroacetone, 1,1-trichloroethane, 1,4-diaminobutane, 1,4-diaminobutane, 1-heptene, 1-methylpyrrole, 1-nonene, 1-octanol, 2-octanol, 3-octanol, 4-octanol, 1-octen-3-one, 1-octene, 1-penten-3-one, 2,3-butanedione, 2,3-hexanedione, 2-amino-pyridine, 2-decanone, 2-heptanone, 2-hexanone, 2-methyl-3-pentanone, 2-methylfuran, 2-nonanone, 2-nonanone, 1-octanol, 2-octanone, 2-pentanone, 3,4-hexanedione, 3-buten-2-one, 3-heptanone, 3-hexanone, 3-hydroxy-2-butanone, 3-methyl-2-pentanone, 3-nonanone, 3-nonen-2-one, 3-octene-2-ol, 3-pentanone, 3-penten-2-one, 4-decanone, 4-heptanone, 4-hexen-3-one, 4-methyl-2-pentanone, 5-methyl-3-hexen-2-one, 5-nonanone, 6-methyl-5-hepten-2-one, acetaldehyde, acetonitrile, acetphenone, benzaldehyde, benzonitrile, bromoform, butanal, butanone, buten-2-one, carbon disulfide, carbon tetrachloride, chloroform, diethyl disulfide, diethyl ether, diethyl phthalate, dimethoxymethane, dimethyl disulfide, dimethyl trisulfide, dimethylsulfoxide, ethanol, ethyl lactate, ethyl pyruvate, ethylvinyl sulfide, formaldehyde, furfuryl alcohol, indole, isobutanal, isoprene, linalool, methanol, methyl butyrate, methyl lactate, methyl pyruvate, methyl-2-hexanone, methyl-3-octanone, methylene chloride, methylpropyl disulfide, nonanal, octene, p-cresol, phenylacetonitrile, phorone, pinene, tetrachloroethylene, thiolactic acid, thiophene, thiourea, toluene, turpentine, or combinations thereof.

19. The method of claim 11, wherein the aqueous acid solution further comprises an organic insect attractant, chosen from 6-methyl-3,5-heptadiene, 1,1,2-trichloroethane, 1,1,3-trichloroacetone, 1,1-trichloroethane, 1,4-diaminobutane, 1,4-diaminobutane, 1-heptene, 1-methylpyrrole, 1-nonene, 1-octanol, 2-octanol, 3-octanol, 4-octanol, 1-octen-3-one, 1-octene, 1-penten-3-one, 2,3-butanedione, 2,3-hexanedione, 2-amino-pyridine, 2-decanone, 2-heptanone, 2-hexanone, 2-methyl-3-pentanone, 2-methylfuran, 2-nonanone, 2-nonanone, 1-octanol, 2-octanone, 2-pentanone, 3,4-hexanedione, 3-buten-2-one, 3-heptanone, 3-hexanone, 3-hydroxy-2-butanone, 3-methyl-2-pentanone, 3-nonanone, 3-nonen-2-one, 3-octene-2-ol, 3-pentanone, 3-penten-2-one, 4-decanone, 4-heptanone, 4-hexen-3-one, 4-methyl-2-pentanone, 5-methyl-3-hexen-2-one, 5-nonanone, 6-methyl-5-hepten-2-one, acetaldehyde, acetonitrile, acetphenone, benzaldehyde, benzonitrile, bromoform, butanal, butanone, buten-2-one, carbon disulfide, carbon tetrachloride, chloroform, diethyl disulfide, diethyl ether, diethyl phthalate, dimethoxymethane, dimethyl disulfide, dimethyl trisulfide, dimethylsulfoxide, ethanol, ethyl lactate, ethyl pyruvate, ethylvinyl sulfide, formaldehyde, furfuryl alcohol, indole, isobutanal, isoprene, linalool, methanol, methyl butyrate, methyl lactate, methyl pyruvate, methyl-2-hexanone, methyl-3-octanone, methylene chloride, methylpropyl disulfide, nonanal, octene, p-cresol, phenylacetonitrile, phorone, pinene, propanoic acid, tetrachloroethylene, thiolactic acid, thiophene, thiourea, toluene, turpentine, or combinations thereof.

20. The method of claim 11, wherein the powder comprising further comprises an anti caking agent chosen from silicon dioxide, aluminum oxide, boron nitride, calcium chloride, magnesium sulfate, calcium bentonite, sodium bentonite, sodium alumino-silicate, magnesium carbonate, calcium silicate, tricalcium phosphate, talc, kaolin, starch, cellulose or combinations thereof.

* * * * *